United States Patent [19]

Corti et al.

[11] Patent Number: 5,145,789
[45] Date of Patent: Sep. 8, 1992

[54] DEVICE AND METHOD FOR PREGNANCY DETECTION

[75] Inventors: Angelo Corti; Paola Piro; Emanuela Carta; Cesare Rovelli; Rosangela Bassi; Sandro Lamponi; Nicola Morgese; Carlo Rurali; Sergio Tognella, all of Milan, Italy

[73] Assignee: Boehringer Biochemia Robin S.p.A., Milan, Italy

[21] Appl. No.: 416,786

[22] Filed: Oct. 5, 1989

[30] Foreign Application Priority Data

Oct. 6, 1988 [IT] Italy .................. 22206 A/88

[51] Int. Cl.$^5$ ........................... G01N 33/548
[52] U.S. Cl. ..................... 436/530; 436/525; 436/531; 436/810; 436/814; 436/818; 435/970; 422/60; 422/61; 422/101; 422/58
[58] Field of Search ............... 436/525, 530, 531, 518, 436/814, 818, 810; 435/810, 970; 422/55, 56, 57, 58, 59, 61, 60, 101

[56] References Cited

U.S. PATENT DOCUMENTS

| | | | |
|---|---|---|---|
| 4,690,907 | 9/1987 | Hibino et al. | 436/518 X |
| 4,916,056 | 4/1990 | Brown, III et al. | 435/810 X |
| 4,999,285 | 3/1991 | Stiso | 422/70 X |

FOREIGN PATENT DOCUMENTS

| | | |
|---|---|---|
| 0258963 | 3/1988 | European Pat. Off. |
| 0299428 | 1/1989 | European Pat. Off. |

Primary Examiner—Esther L. Kepplinger
Attorney, Agent, or Firm—Nikaido, Marmelstein, Murray & Oram

[57] ABSTRACT

A device to determine human chorionic gonadotropin (hCG) in urine is described. It includes:
a) a first area, consisting of a material able to draw urine by capillarity, on which an hCG bioselective colored agent is absorbed, an end of said first area, to be dipped in urine, while the other end contacts with the following b) area;
b) a reading area which contacts the previous one and an area of a material able to assure the capillary flow of urine, on which there is bound:
  1) a protein able to selectively bind hCG and possibly;
  2( hCG (positive reagent control) and
  3) an inert protein (negative reagent control) disposed so as to form, after the reaction with the bioselective colored reagent present in a), two different figures which can be visually detected according to the positivity of the analysis:
c) a further area, an end of which contacts the previous one, of a material able to assure the capillary flow of urine towards the other end containing an indicator revealing the occurred passage of urine through the A device.

According to the invention, pregnancy analysis becomes easier because the a device is dipped just once in the sample to be tested and because the results are simple to read.

9 Claims, 1 Drawing Sheet

DEVICE AND METHOD FOR PREGNANCY DETECTION

The present invention relates to a device and a method for the detection of human chorionic gonadotropin (hCG) in urine for early pregnancy diagnosis.

Human chorionic gonadotropin (hCG) is a glycoprotein hormone synthesized by the placenta and released in blood and urine soon after the implantation of a fertilized ovum in the chorionic tissue.

Concentration of hCG in urine increases from undetectable levels to 50 International Units/l 2-3 weeks after conception and up to 100.000 IU/l after 10 weeks (Speroff L., Glass R. H., Kase N. G.. In "Clinical Gynecologic Endocrinology and Infertility", 3rd ed., Williams and Wilkins Co., Baltimore, 1983:555). For this reason urinary hCG is generally considered a specific marker of pregnancy.

The diagnosis of pregnancy as early as possible is particularly important especially when women are exposed, for therapeutic or professional reasons, to chemical or physical agents, or when, for other health or safety reason, the pregnancy should be interrupted.

Particular efforts were addressed in the last 20 years to develop simple tests to allow unskilled people to make their own pregnancy diagnosis at home, thus avoiding psychological and practical problems connected with bringing urine samples to diagnostic laboratories soon after the missed menses period.

Since the risk of making errors by untrained users increases with the number of operations and reagents needed, it is highly desirable to make available pregnancy tests simpler than those so far developed. The ideal test should be characterized by an analytical device which is simply dipped into urine, without sampling and pipetting operations or time-fixed incubations, followed by a rapid and unequivocal visual reading of results,. preferably in the form of plus/minus signs, including positive and negative controls of reagents, with sufficient sensitivity to detect hCG levels one-two days after the missed menses period (50 IU/L). At the present time several types of pregnancy tests have been developed and/or marketed but none completely fulfills the need of an ideal home test. Moreover, it should be kept in mind that though the accuracy of the assays described so far is generally claimed to be superior to 99%, when carried out by trained laboratory personnel, this could not be true when the assay is performed at home by untrained users. (J. N. Hicks, Losefsohn M. Clinical Chemistry Vol. 34, 1182 (1988)).

Pregnancy detection methods presently in use, are in large part, based on ELISA techniques. This kind of analysis is generally based on a bioselective adsorption on a solid phase coated with anti-hCG antibodies (plastic tubes, balls, rods, membranes etc.) of urine samples previously mixed and incubated with other anti-hCG antibodies labelled with enzyme probes or labels. The immunological reaction is then developed, after appropriate washings, by an enzymatic reaction with chromogen substrates. Although immunoenzymatic tests are generally very sensitive and rapid, they require several operations.

Moreover some of these need particular care, e.g. the washing steps, which can cause "false positives" if not correctly done. Moreover the tendency of the enzyme probe or label to inactuate during storage and analysis may represent another potential source of errors in immunoenzymatic tests.

EP-A- No. 243370 discloses immunoenzymatic assays based on particular devices able to help the user; yet some of the above mentioned disadvantages are still present (colors involving error or confusion possibilities in the interpretation of the results, lack of positive and negative reagent controls, impossibility to keep the analysis results for a comparison with the tests carried out subsequently, etc).

Other types of immunoassay have been reported so far having different advantages and disadvantages with respect to ELISA techniques. Great value was shown by assays relying on the use of immunoreactants labelled with directly visible colored cells or particles without extra enzymatic reactions. First to be developed as visually detectable labels were red blood cells used in hCG haemagglutination tests, introduced in the early 60's by Wide and Gemzell (Wide L., Gemzell C. A. Acta Endocrinol. 35, 261 (1960); Wide L. Acta Endocrinol. 70, 1-111, (1962). This test is based on the agglutination of sheep hCG-coated red blood cells caused by immunoreaction with rabbit anti-hCG antiserum. The inhibition of this reaction by the hCG present in the urine sample is indicated by characteristic ring pattern at the bottom of the test tube. Similar methods, based on the use of latex particles are described, for example, in EP-A No. 1561920, Israel Patent No. 50929 and Israel Patent No. 47223.

Other direct reading methods so far described rely on the use of antibodies labelled with stained bacteria (EP-A No. 0074520), with colloidal metals (Leuvering, J. H. W. et Al., J. Immunoassay 1, 77 (1980)) or hydrophobic organic dyes (EP-A No. 0032270). Some of these "direct reading" assays are of great value for home pregnancy tests since they fulfill the need of maximum simplicity (one step without washings) and good sensitivity, but they still suffer from a number of shortcomings such as the requirement of long fixed-time incubations, sampling operations, the need of color estimation or comparison that is often difficult for untrained users (positive and negative results appearing as plus/minus signs are by far more unequivocal and preferable) and do not provide a built-in positive and negative control of reagents in the same assay device.

Most of these shortcomings have been overcome by the colloidal gold membrane assay (COGMA) described in EP-A-0258963 and EP-A-0254081. This assay combines the rapidity of membrane immunoconcentration ELISA techniques with the simplicity of assays relying on visually detectable probes (no need of washing steps and chromogenic reactions). As described for example in EP-A No. 0254081, pregnancy tests can be carried out in a few minutes with four operations: 1) the urine sample to be tested is pipetted into a filtration apparatus located above a membrane carrying an anti-hCG antibody, 2) the urine sample is left to absorb through the filter and membrane by means of a physically absorbent material contacted with the lower part of the membrane, 3) the filtration apparatus is removed, 4) a second gold labelled anti-hCG antibody is then pipetted and left to absorb through a membrane A reddish spot is observed immediately at the center of the membrane when urine contains no more than 5 IU/l of hCG.

EP-A-0258963 describes a pregnancy test completely similar in principle to that described in EP-A 0254081 except for the final results which are obtained in a more unequivocal form of plus/minus signs.

EP-A 0250137 describes a different form of colloidal gold membrane assay for quantitative measurement of various analytes, also appliable for pregnancy detection. The sample and the gold-labelled reagent are mixed and then contacted with one end of a membrane strip carrying the binding reagent as horizontal band and allowing upward flow through a membrane. The height of the visually observable color may be correlated to the presence of the ligand to be determined in the fluid sample. However, though this assay gives quantitative information, it does not seem to provide remarkable advantages for home qualitative hCG tests and more important, the results are not obtained as plus/minus spots which are preferable for unskilled users.

Though the colloidal membrane assays represent a remarkable advantage in home pregnancy test, they do not completely fulfill the need of an ideal test which should not involve pipetting, urine sampling and filtering operations.

The use of reagent impregnated test-strips in specific binding assays, has previously been proposed, for example, in EP-A 0225054 (WO-A 8702774), U.S. Pat. No. 4,624,929, EP-A 0217406 and EP-A 0291194.

It is an object of the present invention to provide an analytical device and method for a more simple and reliable pregnancy detection by unskilled users. The method and the device are characterized by the following advantages over the previously described assays and methods:

a) they do not require filtering operations;
b) they do not require pipetting operation;
c) they do not require time measurements;
d) they do not require exact volume measurements;
e) they do not require washing steps;
f) they require only one simple dipping operations;
g) they are rapid (require no more than 3-5 minutes);
h) they have a high detectability (detection limit, 100 U/l);
i) they do not contain additional liquid reagents, avoiding any possible confusion;
l) they allow long storage of results without bleaching allowing comparisons with tests carried out afterward;
m) they provide a built-in positive and negative control of reagents and assay performance;
n) they allow unequivocal visual reading of results in the form of plus/minus signs.

No assay method so far described present all of these properties combined in the same analytical system.

The above mentioned effects are obtained thanks to the device and the method of the invention, based on the principle of sandwich reactions between hCG and a couple of biospecific hCG binding reagents, one of which is immobilized in a particular part of the reading area of the device and the other labelled with visually detectable compound or particle. The device according to the invention comprises:

a) a first area, consisting of a material able to draw urine by capillarity, on which an hCG bioselective colored agent is absorbed, an end of said first area to be dipped in urine, while the other end contacts the following b) area;
b) a reading area which contacts the previous one and an area of a material able to assure the capillary flow of urine, on which there is bound:
1) a protein able to selectively bind hCG and possibly;
2) hCG (positive reagent control) and
3) an inert protein (negative reagent control), said hCG and inert protein disposed so as to form, after the reaction with the bioselective colored reagent present in
a), two different figures which can be visually detectable according to the positivity of the analysis;
c) a further area, an end of which contacts the previous one, of a material able to assure the capillary flow of urine towards the other end containing an indicator revealing the occurred passage of urine through the device.

The areas b) and c) together constitute an element which can be called "immunoconcentrator" element while the a) area constitutes a compartment wherein the bioselective colored reagent is present in a preabsorbed state on an appropriate supporting material, from which it is made available by the capillary flow of urine under exam.

According to the present invention the colored reagent comprises an hCG-biospecific binding reagent able to form sandwich complexes with hCG and other hCG-binding reagents immobilized on the reading area, labelled with a visually detectable compound, particle, or cell. Examples of hCG binding reagents which can be used in a labelled form are monoclonal and polyclonal antibodies or lectins (Concanavalin A, wheat germ lectin, lentil lectin and soy bean lectin) selected for their capability of making sandwich complexes with hCG and other hCG-binding reagents immobilized onto the reading area, e.g. by binding to different epitopes or sites on the hCG molecules. Several methods are known for labelling immunoreactants with visually detectable tags. This type of label may include stained bacteria (e.g. killed stained Staphylococci), colored latex particles, hydrophobic dyes, colloidal metals able to bind proteins when adjusted to the optimal pH and concentration (gold, silver, platinum, copper, and the metal compounds sodium hydroxide, silver iodide, silver bromide, copper hydroxide, aluminium hydroxyde, chromium hydroxide, vanadium oxide, arsenic iodide, manganese hydroxyde and the like). Methods for coupling colored particles to proteins are already known and well described in the above cited references.

Preferred colored tag for immunoreactants in the present invention are colored particles with a diameter size lower then 200 nm.

The preferred bioselective colored reagents are monoclonal or polyclonal anti-hCG antibodies labelled with colloidal gold, recently commercially available. The size of the colloidal metal particle is preferably from 5 to 100 nm.

Said colored bioselective reagent is adsorbed on a supporting material which has capillary properties and is able to assure the elution of the colored bioselective reagent thanks to the action of the capillary forces at the urine passage. A cellulose or cellulose powder absorbing filter is useful for this purpose.

The reading area consists of a membrane or filter able to bind proteins, such as nitrocellulose, nylon, Immunodyne, Biodyne, cyanogen bromide, activated paper with pore size ranging from 0.45 to 12 $\mu$m, preferably from 0.45 to 1.2 $\mu$m.

Examples of hydrophylic capillary materials are paper, cellulose powder cotton or other cellulose derivatives, hydrophylic polymers, polysaccharides or polyols, kaolin, titanium dioxide, barium sulfate, and diatomaceous earth.

The flow indicator which is present on the upper part of said material is, for instance, a pH indicator compound able to change color when wetted by urine, for instance bromophenol blue. The device of the invention can be shaped in several forms suited for the intended use, for instance as a stick, small tube, strip-supported on plastic material, paper or the like.

In the preferred embodiments of the invention the "reading area" consists of a piece of 0.5-2 $cm^2$ of commercially available filter paper containing nitrocellulose or other mechanically strong protein binding membrane, contacted with the lower part of a cellulose absorbent stick, containing in the upper part a pH-indicator compound. The nitrocellulose filter and the absorbent stick are tightly sealed with a plastic material leaving a part of the nitrocellulose filter free to contact the area a). Also the upper part of the immunoconcentrator stick is left free.

hCG, an anti-hCG mono or polyclonal antibody and an inert protein, as described herinafter, are bound on the nitrocellulose filter. The stick is then introduced in an appropriate container, in which the biospecific colored reagent absorbed at a dry state on a cellulose material, is contained, so that the visually detectable nitrocellulose membrane contacts it.

This nitrocellulose membrane is structurally divided in three areas: the first area (herein after referred as 1A) carries immobilized hCG; the second area (herein after referred as 1B) carries an anti-hCG monoclonal or polyclonal antibody; and the third area (herein after referred as 1C) carries an inert protein, that is bovine serum albumine.

Alternatively other proteins can be used in the three areas: for example hCG-binding lectins can be used instead of monoclonal or polyclonal antibodies in 1B; casein, fatty acid free milk, ovalbumin, gelatin, non immune sera or any other inert protein can be immobilized instead of bovine serum albumine in 1C. The proteins can be immobilized according to methods well known to the man skilled in the art or by following the membrane manufacturer's instructions. Protein solutions can be simply dropped onto the relevant area or sprayed in narrow bands using a TLC quantitative sample applicator.

The invention is now described with reference to the enclosed drawings, wherein:

FIG. 1b is an enlarged view of the device of FIG. 1a.

Figure 1B:
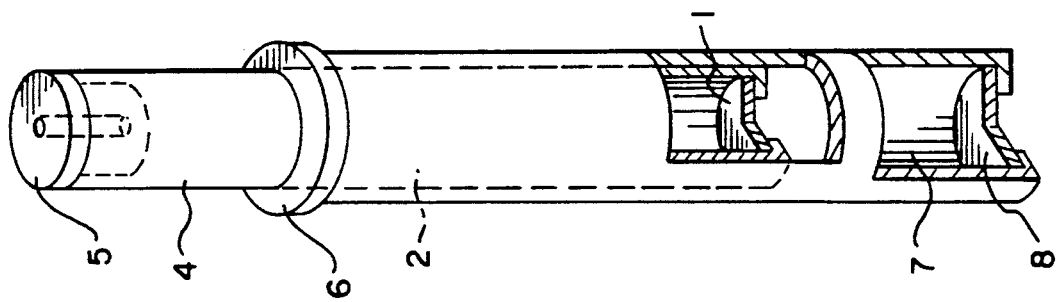

In the above mentioned Figures, the reference number 1 shows the nitrocellulose filter, and areas 1A, 1B and 1C; the reference number 2 indicates the hydrophilic material which assures the capillary flow of urine, while the reference 3 shows the area of the same material 2 on which a pH indicator was left to adsorb. Number 4 indicates the plastic envelope constituting the stick. Number 5 shows an opened, inert element which closes the upper part of the device.

Finally, number 6 shows the container where the colored biospecific reagent, adsorbed on cellulosic material 7, is present. The container number 8 presents an hydrophilic pore sectum, which closes a hole of container 6 to be dipped in the urine sample when the analysis is carried out.

Therefore the only requested operations are the immersion of the device in urine until area 3 changes color, showing that the device was filled with urine, and the following removal of the stick with a visual inspection of the nitrocellulose membrane.

Figure 1A:
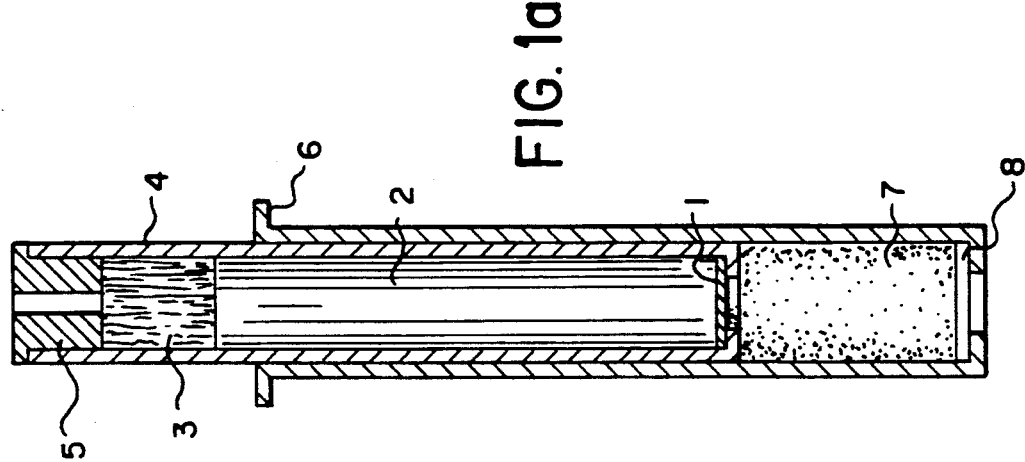
FIG. 1a shows an embodiment of the device of the invention as seen in a longitudinal section.
Figure 1C:
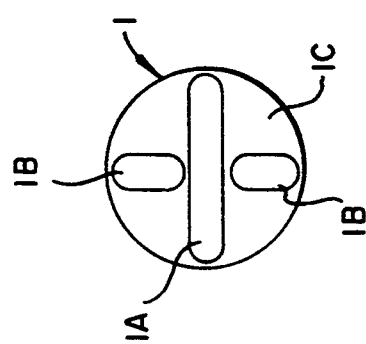
FIG. 1c is a view from the top of the nitrocellulose filter which constitutes the reading area of the device.

Results are read as follows:

staining of 1B is indicative of pregnancy; unstaining is indicative of non-pregnancy 1A and 1C are control areas for reagents and assay performance. In particular 1A must always stain (positive control) while 1C must never stain (negative control). Preferred forms of the final colored signals are a plus sign (+) for pregnancy and a minus sign (−) for non pregnancy. This can be obtained for example by dividing the reading areas in 1A, 1B, and 1C as depicted in FIG. 1. 1A (positive control, horizontal tract) always stains independently on the presence of hCG in urine, 1B (test area, vertical tract) stains only when hCG is present in urine; 1C (negative control, surrounding area) never stains independently of the presence of hCG in urine.

The invention also refers to a method for the determination of hCG in urine, in which urine is contacted with:

a) an hCG bioselective colored reagent adsorbed at dry state on a material which allows the capillary flow of urine;

b) a membrane of nitrocellulose or other material able to strongly bind proteins on which a protein able to selectively bind hCG and possibly hCG and a different protein are irreversibly bound;

c) an hydrophilic material on which a pH indicator is preferably adsorbed.

The method which is object of the present invention is based, in detail, on the use of the device described hereinbefore, which allows the pregnancy analysis with just one dipping operation and a subsequent direct and clear reading of the results. The method and the device of the invention allow the pregnancy analysis in a few minutes and with a sensitivity equal to that of the best systems available up to now. The device of the invention can be part of a kit which, for instance, consists in a urine container endowed with a support for the analytical device. Moreover, this kit has instructions to carry out pregnancy analysis in accordance with the invention. The following Example illustrates the present invention in a non-limitative way.

EXAMPLE

Materials. The following materials were used: colloidal gold particles, 15 nm, (Janssen Life Sciences Products, Olen, Belgium), nitrocellulose, 0.45 μm, supported on filter paper (1 mm thick) (Chemetron Laboratories, Milan, Italy); human chorionic gonadotropin, 5000 IU/mg, (Prodas s.r.l., Milan, Italy); bovine serum albumine (Sigma Chemical Co., St Louis, Mo. 63178); cellulose powder; anti-hCG (β-subunit) monoclonal antibodies Mab B2, Mab A1 and Mab C3 were obtained by Boehringer Mannheim Milano, Italy.

All the other reagents were analytical grade products by Merck (Darmstad, FRG) or Carlo Erba (Milano, Italy).

Preparation of the analytical device.

A) Preparation of immunoconcentrator dip-stick.

Round pieces of nitrocellulose filters (0.9 cm, diameter) were washed for 10 minutes with distilled water and air dried for 15 minutes. Then 3 µl aliquotes of a 0.1 mg/ml hCG solution (5000 IU/mg) in 3 mM potassium chloride, 136 mM sodium chloride, 10 mM sodium phosphate buffer (PBS), pH 7.4 were applied onto the filter surface by using particular plastic applicators prepared as follows: polystyrene plastic sticks (80 mm×1 mm×7 mm) were carved longitudinally on the base (0.3 mm deep) and slightly dipped into the hCG solution. About 3 µL of hCG were withdrawn by capillary forces in the carved surface of each plastic stick. Then the withdrawn solutions were dot blotted onto the nitrocellulose filters simply by touching the filters with the plastic sticks. Since the binding is rapid, the hCG spots on each filter resulted as rectangles of about 7 mm×1 mm. The filters were washed twice with PBS and air dried. Similarly 2 µl aliquotes of a 1 mg/ml Mab B2 solution in PBS were applied to each piece of nitrocellulose filter forming a cross with the "hCG area", as described in FIG. 1. The filters were left to dry for 15 min and blocked by incubation for 30 min with a 10% BSA solution in PBS at room temperature. Then each filter was washed twice with PBS, left to dry for at least 15 min. In parallel, the top of cellulose cylindric absorbent filters (diameter, 0.9 cm; height, 10 cm) was dipped into bromophenol blue solutions in 0.01 M HCl and left to absorb and dry at room temperature. This compound, yellowish under these conditions, turns blue when the filter is wetted by urine during the assay.

After drying, both nitrocellulose membranes and absorbent filter were assembled in a cylindric transparent polyethylene plastic container (internal diameter 0.9 cm, height 10 cm) as depicted in FIG. 1. The filters were pressed in order to ensure complete and uniform contact between nitrocellulose filter and absorbent cellulose filter and fixed on the top with a plugs having a hole (1 mm, diameter) in the center, to ensure air outlet and the capillary upflow of urine during the pregnancy test.

B) Preparation of gold-labelled anti-hCG antibodies

Compartment. The anti-hCG Mab C3, Mab B2, Mab A1 were labelled with colloidal gold particles of 15 nm, at pH 6, according to the manufacturer's instructions (Janssen Life Products, Beerse, Belguim). The final products were centrifuged for 30 min at 12,000 g and resuspended in 0.15 M sodium chloride, 0.02 M TRIS-HCl buffer, pH 8.2, containing 200 g/L glycerol, 10 g/L BSA and 20 mM sodium azide, diluted with the same buffer at 4.0 Optical Density units (520 nm), and kept a 4° C. until use.

The various gold-labelled monoclonal antibodies were tested for: a) their capability to form visually detectable sandwich complexes with hCG (0.5 U) and Mab B2 antibody immobilized on the nitrocellulose filters as described above; b) binding to hCG directly immobilized on the nitrocellulose filter; c) binding to nitrocellulose blocked with BSA. The results showed that sandwich complexes with hCG and Mab B2 were obtained with all gold labelled antibodies. However Mab AC-Gold was unable to bind hCG directly immobilized on nitrocellulose and because the most visually detectable signal was obtained with Mab C3-Gold conjugate. Thus this gold labelled antibody was selected for the preparation of the "gold labelled antibody compartment" of the device.

0.5 g of cellulose powder portions were presaturated for 2 h at 37° C. with 1% BSA and washed twice with TBS by repeated centrifugation and resuspension. Then the powder was dried at 37° C., mixed with 0.5 ml aliquotes of Mab C3 gold conjugate diluted 1:10 with TBS, and dried again at 37° C. The powder obtained was used to fill a polyethylene plastic tube having a filter on the bottom.

The immunoconcentrator dip-stick and the gold labelled antibody compartment were assembled as depicted in FIG. 1.

C) Detection of hCG in urine

The analytical devices prepared as described above, were dipped in urine or standard samples until the indicator area changed color (about five minutes). Then the immunoconcentrator sticks were removed from the device for inspection of the "reading area". Results, appearing as red plus/minus signs, were visually evaluated.

D) Detectability and accuracy. In order to evaluate the detectability and the accuracy of this assay we have added increasing amounts of hCG to urine samples of non-pregnant women and further analyzed Urine samples containing more than 100 U/l produced a "plus" sign clearly distinct from the "minus" sign obtained in the absence of hCG. Moreover, when we repeated 10 times the assay of the urine sample containing 100 Ul, we obtained in all cases positive results indicating that 100 U/L can be assumed as "cut-off" limit for positive and negative results. In order to further evaluate the accuracy of pregnancy detection, 49 samples of urine from pregnant women and 52 samples from non-pregnant women (total: 101 samples of urine) were tested according to the method of the present invention. As shown in Tab. 1, the results observed were identical to those expected indicating that the assay of the invention is satisfactorily accurate.

TABLE

| Detection of hCG in urines from pregnant and non-pregnant women | | | |
|---|---|---|---|
| Pregnant (a) (Positive, N.o) | | Non-pregnant (a) (Negative, N.o) | |
| Expected | Observed | Expected | Observed |
| 49 | 49 | 52 | 52 |

(a) Pregnancy was detected in parallel by using the Event Test Color Kit (Boehringer Biochemia Robin, Italy).

We claim:

1. A device to detect human chorionic gonadotropin (hCG) in urine, comprising:
   a first longitudinal container having distal and proximal ends, said distal end of said first container containing a hydrophilic pore septum which covers an entrance in said distal end through which urine is capable of being drawn;
   a second longitudinal container having distal and proximal ends, said second container being telescopically housed within and capable of being removed from said first container;
   a first material contained within an area defined between said hydrophilic pore septum and said distal end of said second container, said first material capable of drawing urine by capillarity and on which a color labeled first protein capable of specifically binding to hCG is diffusively adsorbed;

a second material comprising a reading area contained within the distal end of said second container and in contact with said first material to allow movement of urine from said first material through said second material and on which is bound (i) a second protein capable of specifically binding to hCG, wherein at least one of said first or second protein is an antibody, (ii) immobilized hCG and (iii) an inert protein, wherein (i), (ii), and (iii) are disposed on said second material so as to form, after reaction with said first color labeled protein, at least one of two figures which can be visually detected according to the positivity of the reaction when the second container is removed from the first container;

a third material capable of drawing urine by capillarity contained within the proximal end of said second container and contacting said second material to allow movement of urine through said second material to said third material; and a flow indicator means contained within said third material at the proximal end of said second container, said means capable of indicating the passage of urine through said device.

2. The device according to claim 1, wherein said color labeled first protein is a monoclonal antibody labeled with colloidal gold.

3. The device according to claim 1, wherein said second protein capable of specifically binding to hCG is a monoclonal antibody.

4. The device according to claim 1, wherein said second material is a nitrocellulose filter.

5. The device according to claim 1, wherein said first material and said third material are cellulosic.

6. The device according to claim 1, wherein said flow indicator means is a compound which changes color upon contact with urine.

7. The device according to claim 6, wherein said compound is bromophenol blue.

8. The device according to claim 1, wherein said at least one of two figures which can be visually detected according to the positivity of the reaction is a plus (+) sign or a minus (−) sign.

9. A method of detecting human chorionic gonadotropin (hCG) in urine, comprising the steps of:

(a) providing a capillary device, wherein said capillary device contains therein:

a first longitudinal container having distal and proximal ends, said distal end of said first container containing a hydrophilic pore septum which covers an entrance in said distal end through which urine is capable of being drawn;

a second longitudinal container having distal and proximal ends, said second container being telescopically housed within and capable of being removed from said first container;

a first material contained within an area defined between said hydrophilic pore septum and said distal end of said second container, said first material capable of drawing urine by capillarity and on which a color labeled first protein capable of specifically binding to hCG is diffusively adsorbed;

a second material comprising a reading area contained within the distal end of said second container and in contact with said first material to allow movement of urine from said first material through said second material and on which is bound (i) a second protein capable of specifically binding to hCG, wherein at least one of said first or second protein is an antibody, (ii) immobilized hCG, and (iii) an inert protein, wherein (i), (ii), and (iii) are disposed on said second material so as to form, after reaction with said first color labeled protein, at least one of two figures which can be visually detected according to the positivity of the reaction when the second container is removed from the first container;

a third material capable of drawing urine by capillarity contained within the proximal end of said container and contacting said second material to allow movement of urine through said second material to said third material; and a flow indicator means contained within said third material at the proximal end of said second container, said means capable of indicating the passage of urine through said device;

(b) contacting the distal end of said capillary device with a urine sample suspected of containing hCG, and allowing said sample to migrate into said capillary device by capillary action, thereby subjecting any hCG present in said sample to immunoreaction with said color labeled first protein capable of specifically binding to hCG in said first material to form a labeled immunocomplex, followed by further migration of said immunocomplex onto said second material, wherein any immunocomplex is bound to said second protein capable of specifically binding to hCG;

(c) removing said second container from said first container; and (d) visually detecting said at least one of two figures to determine if hCG is present in said urine sample.

* * * * *